United States Patent [19]

Freyne et al.

[11] Patent Number: 5,602,134

[45] Date of Patent: Feb. 11, 1997

[54] POSITIVE INOTROPIC AND LUSITROPIC PYRROLOQUINOLINONE DERIVATIVES

[75] Inventors: Eddy J. E. Freyne, Rumst; Alfons H. M. Raeymaekers, Beerse, both of Belgium

[73] Assignee: Janssen Pharmaceutica N.V., Beerse, Belgium

[21] Appl. No.: 553,580

[22] PCT Filed: Jun. 15, 1994

[86] PCT No.: PCT/EP94/01960

§ 371 Date: Nov. 29, 1995

§ 102(e) Date: Nov. 29, 1995

[87] PCT Pub. No.: WO95/00512

PCT Pub. Date: Jan. 5, 1995

[30] Foreign Application Priority Data

Jun. 21, 1993 [EP] European Pat. Off. .............. 93201771

[51] Int. Cl.[6] .......................... A01N 43/38; A01N 43/42; C07D 471/02

[52] U.S. Cl. .......................... 514/253; 514/292; 544/295; 544/361; 544/372; 546/84; 546/208; 546/210; 548/546; 548/547

[58] Field of Search ..................... 544/295, 361, 544/372; 546/84, 208, 210; 548/546, 547; 514/292, 253

[56] References Cited

U.S. PATENT DOCUMENTS

| | | | |
|---|---|---|---|
| 4,943,573 | 7/1990 | Meanwell et al. | 514/253 |
| 5,196,428 | 3/1993 | Meanwell et al. | 514/253 |
| 5,220,023 | 6/1993 | Freyne | 544/165 |

OTHER PUBLICATIONS

Evans et al., Screening and Determination of Kinetic Parameters of Aromatase inhibitors using Human Genital Skin Fibroblasts, Journal of Enzyme Inhibition, 1993, vol. 7, pp. 203–212 1993.

*Primary Examiner*—Mukund J. Shah
*Assistant Examiner*—Deepak Rao
*Attorney, Agent, or Firm*—Charles J. Metz

[57] ABSTRACT

The present invention relates to novel positive inotropic and lusitropic compounds of formula

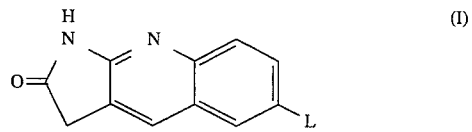

the pharmaceutical acceptable acid addition salts thereof and the stereochemically isomeric forms thereof wherein L is a radical of formula —O-Alk-$(NH)_p$-C(=O)-$R^1$, pharmaceutical compositions thereof, methods of preparing said compounds and intermediates in the preparation thereof.

14 Claims, No Drawings

POSITIVE INOTROPIC AND LUSITROPIC PYRROLOQUINOLINONE DERIVATIVES

CROSS-REFERENCE TO RELATED APPLICATIONS

This application is based upon PCT Application Ser. No. PCT/EP 94/01960, filed Jun. 15, 1994, which claims priority from European Patent Application Ser. No. 93.201.771.8, filed on Jun. 21, 1993.

EP-0,406,958 describes imidazoquinazolinone derivatives having positive inotropic and lusitropic properties. GB-2,190,676 and EP-0,426,180 disclose a number of imidazoquinolinones as c-AMP phosphodiesterase inhibitors. U.S. Pat. No. 5,196,428 describes imidazoquinolinones having an inhibitory effect on the ADP induced blood platelet aggregation in human platelet-rich plasma.

Perkin and Robinson, J. Chem. Soc., 103, 1973 (1913) describe the preparation of 1,3-dihydro-2H-pyrrolo[2,3-b]quinolin-2-one. However, according to Tanaka et al., J. Het. Chem., 9, 135 (1972) the procedure of Perkin and Robinson did not produce the above pyrroloquinolinone compound, but rather some plain quinoline derivatives.

Vogel et al., Helv. Chim. Acta., 52(7), 1929 (1969) and U.S. Pat. No. 3,974,165 describe the preparation of some partially hydrogenated pyrrolo[2,3-b]quinolin-2-one derivatives.

The compounds of the present invention differ structurally from the cited art-known compounds by the particular substitution of the pyrroloquinolinone moiety and by their favorable positive inotropic and lusitropic properties.

The present invention is concerned with novel 1,3-dihydro-2H-pyrrolo[2,3-b]-quinolin-2-one derivatives having the formula

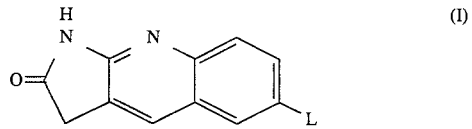

the pharmaceutically acceptable addition salts thereof and the stereochemically isomeric forms thereof, wherein L is a radical of formula —O-Alk-(NH)$_p$-C(=O)-R$^1$, wherein Alk is C$_{1-6}$alkanediyl;

p is 0 or 1; and

R$^1$ is hydroxy, C$_{1-4}$alkyloxy or —NR$^2$R$^3$, wherein

R$^2$ is hydrogen or C$_{1-4}$alkyl; and

R$^3$ is C$_{3-7}$cycloalkyl or piperidinyl, which is optionally substituted with C$_{1-4}$alkyl, phenylmethyl or C$_{3-7}$cycloalkylmethyl;

R$^2$ and R$^3$ may also be joined together to form piperazinyl, optionally substituted with C$_{3-7}$cycloalkyl, C$_{3-7}$cycloalkylmethyl, C$_{1-6}$alkyl optionally substituted with one or two hydroxy groups, 2,2-dimethyl-1,3-dioxcilanylmethyl, benzyl, halophenylmethyl, (cyclopentyloxy)(methoxy)phenylmethyl, diphenylC$_{1-4}$alkyl, pyridinyl, pyrimidinyl or phenyl optionally substituted with C$_{1-4}$alkyloxy or halo; or R$^2$ and R$^3$ are joined together to form piperidinyl, optionally substituted with imidazolylcarbonyl.

In the foregoing definitions halo is generic to fluoro, chloro, bromo and iodo; the term C$_{1-4}$alkyl defines straight and branched saturated hydrocarbon radicals having from 1 to 4 carbon atoms, such as, for example, methyl, ethyl, propyl, 1-methylethyl, butyl, 1-methylpropyl, 2-methylpropyl and 1,1-dimethylethyl; C$_{1-6}$alkyl defines C$_{1-4}$alkyl and the higher homologs thereof such as, for example, pentyl, hexyl and the like; C$_{3-7}$cycloalkyl defines cyclopropyl, cyclobutyl, cyclopentyl, cyclohexyl and cycloheptyl; C$_{1-6}$alkanediyl defines straight and branch chained bivalent hydrocarbon radicals having from 1 to 6 carbon atoms such as, for example, methylene, 1,2-ethanediyl, 1,3-propanediyl, 1,4-butanediyl, 1,5-pentanediyl, 1,6-hexanediyl, 1,1-ethanediyl, 1,1-propanediyl, 1,2-propanediyl and the like.

Pharmaceutically acceptable addition salts as mentioned hereinabove comprise the therapeutically active non-toxic addition salt forms which the compounds of formula (I) are able to form. Said salt forms can conveniently be obtained by treating the base form of the compounds of formula (I) with appropriate acids such as inorganic acids, tier example, hydrohalic acid, e.g. hydrochloric, hydrobromic and the like acids, sulfuric acid, nitric acid, phosphoric acid and the like; or organic acids, such as, for example, acetic, propanoic, hydroxyacetic, 2-hydroxypropanoic, 2-oxopropanoic, ethanedioic, propanedioic, butanedioic, (Z)-2-butenedioic, (E)-2-butenedioic, 2-hydroxybutanedioic, 2,3-dihydroxybutanedioic, 2-hydroxy-1,2,3-propanetricarboxylic, methanesulfonic, ethanesulfonic, benzenesulfonic, 4-methylbenzenesulfonic, cyclohexanesulfamic, 2-hydroxybenzoic, 4-amino-2-hydroxybenzoic and the like acids. Conversely the salt form can be converted by treatment with alkali into the free base form.

The compounds of formula (I) containing acidic protons may also be converted into their therapeutically active non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like.

The term addition salt also comprises the hydrates and solvent addition forms which the compounds of formula (I) are able to form. Examples of such forms are e.g. hydrates, alcoholates e.g. ethanolates, and the like.

Pure stereochemically isomeric forms of the compounds of formula (I) may be obtained by the application of art-known procedures. Diastereoisomers may be separated by physical methods such as selective crystallization and chromatographic techniques, e.g. counter current distribution, liquid chromatography and the like; and enantiomers may be separated from each other following art-known resolution methods, for example, by the selective crystallization of their diastereomeric salts with chiral acids. Pure stereochemically isomeric forms may also be derived from the corresponding pure stereochemically isomeric forms of the appropriate starting materials, provided that the reactions occur stereospecifically. As a further alternative, the enantiomers may be separated by liquid chromatography using a chiral stationary phase. Stereochemically isomeric forms of the compounds of formula (I) are obviously intended to be included within the scope of the invention.

Further, the compounds of the present invention may exist in different tautomeric forms and all such tautomeric forms are intended to be included within the scope of the present invention.

Particular compounds of formula (I) are those compounds wherein

L is a radical of formula —O-Alk-C(=O)-R$^1$, wherein

Alk is $C_{1-6}$alkanediyl; and $R^1$ is hydroxy, $C^{1-4}$alkyloxy or —$NR^2R^3$, wherein $R^2$ is hydrogen or $C_{1-4}$alkyl; and $R^3$ is $C_{3-7}$cycloalkyl or piperidinyl, which is optionally substituted with $C_{1-4}$alkyl or phenylmethyl;

$R^2$ and $R^3$ may also be joined together to form piperazinyl, optionally substituted with $C_{3-7}$cycloalkyl, $C_{3-7}$cycloalkylmethyl, $C_{1-6}$alkyl, benzyl, diphenyl$C_{1-4}$alkyl, pyridinyl, pyrimidinyl or phenyl optionally substituted with $C_{1-4}$alkyloxy or halo; or $R^2$ and $R^3$ are joined together to form piperidinyl, optionally substituted with imidazolylcarbonyl.

Preferred compounds of formula (I) are those compounds where $R^1$ is —$NR^2R^3$.

More preferred compounds are those preferred compounds wherein $R^2$ and $R^3$ are joined together to form a piperazinyl substituted with $C_{3-7}$cycloalkylmethyl.

Still more preferred compounds, are those more preferred compounds wherein $R^1$ is 4-(cyclohexylmethyl)piperazinyl.

The most preferred compounds of formula (I) are 1-(cyclohexylmethyl)-4-[4-[(2,3-dihydro-2-oxo-1H-pyrrolo[2,3-b]quinolin-6-yl)oxy]-1-oxybutyl]piperazine and 1-(cyclohexylmethyl)-4-[5-[(2,3-dihydro-2-oxo- 1H-pyrrolo 2,3-b]quinolin-6-yl)oxy]-1-oxopentyl]piperazine, the pharmaceutically acceptable addition salts thereof and the stereochemically isomeric forms thereof.

The compounds of formula (I) can be prepared by reacting an intermediate of formula (II) in the presence of a suitable dehydrogenating reagent in a reaction-inert solvent.

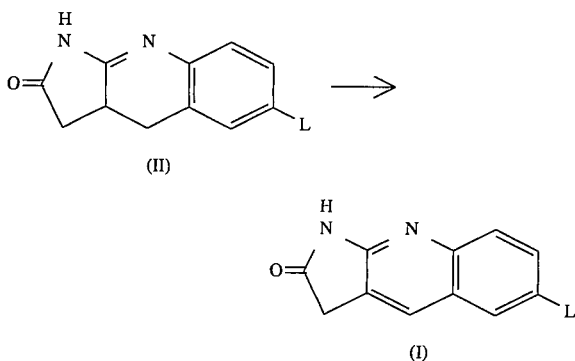

The above reaction may conveniently be conducted using, e.g. 4,5-dichloro-3,6-dioxo-1,4-cyclohexadiene-1,2-dicarbonitrile and the like as a dehydrogenating reagent in tetrahydrofuran, 1,4-dioxane or a mixture of these solvents. Alternatively, the above reaction may be performed in the presence of a suitable catalyst, e.g. platinum on charcoal, palladium on charcoal, in a suitable solvent, e.g. toluene, diisopropylbenzene, xylene, cumene and the like, optionally upon addition of a catalyst poison, e.g. thiophene, and optionally in the presence of a hydrogen acceptor, e.g. 2,5-dimethyl-2,4-hexadiene, cyclohexene and the like. When using a catalyst as described above, the reaction of (II) into (I) is preferably conducted at increased temperature and/or pressure.

The compounds of formula (I) may also be prepared by reacting an intermediate of formula (III) in the presence of a suitable catalyst, e.g. bis(triphenylphosphine)palladium(II)chloride, tetrakis(triphenylphosphine)palladium(0), palladium on charcoal and the like in a suitable solvent, e.g. methylbenzene, acetic acid, propanoic acid, 2-methylpropanoic acid, 2,2-dimethylpropanoic acid and the like.

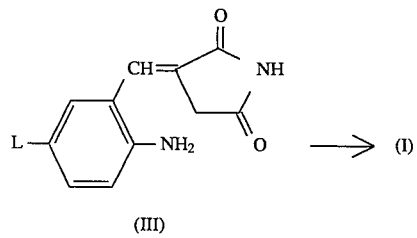

Alternatively, the compounds of formula (I) may be prepared by O-alkylating the corresponding 6-hydroxypyrroloquinolinone compounds or a protected derivative thereof following art-known procedures.

The compounds of formula (I) can also be converted into each other following art-known procedures of functional group transformation, e.g. (trans)esterification, (trans)amidation, and the like methods.

For example, the compounds of formula (I) wherein $R^1$ is hydroxy can be prepared by hydrolyzing the corresponding compounds wherein $R^1$ is $C_{1-4}$alkyloxy, following art-known procedures, e.g. in the presence of a base or an acid.

Further, the compounds of formula (I) wherein $R^1$ is —$NR^2R^3$ can be prepared by reacting the corresponding carboxylic acid with $HNR^2R^3$ in the presence of a suitable reagent capable of forming amides, e.g. diphenyl phosphoryl azide. When using the latter azide compound, the reaction is preferably conducted in the presence of a suitable base, e.g. N,N-diethylethanamine, optionally in the presence of a catalytic amount of N,N-dimethyl-4-pyridinamine, in a reaction-inert solvent, e.g. N,N-dimethylformamide, 1-methylpyrrolidin-2-one and the like. The latter procedure, when conducted at elevated temperatures (preferably at 180°–200° C.) may yield a Curtius like rearrangement reaction as described in J. Med. Chem. 1993, 36, 22, 3252, thus yielding compounds of formula (I) wherein p is 1.

Alternatively, said carboxylic acid may be converted into a suitable reactive functional derivative thereof such as, for example, an acyl halide or an acid anhydride, before reaction with the amine $HNR^2R^3$. Said reactive functional derivatives may be prepared following art known methods, for example, by reacting the carboxylic acid with a halogenating reagent such as, for example, thionyl chloride and the like. An acid anhydride may be prepared by reacting an acyl halide derivative with a carboxylate salt. The functional derivatives described above are characterized by $R^1$ being halo or $C_{1-4}$alkyloxycarbonyloxy.

The compounds of formula (I) wherein $R^2$ and $R^3$ form a piperazinyl group may be prepared by debenzylation of the corresponding phenylmethylpiperazine compound following art known procedures e.g. hydrogenation. The compounds of formula (I) wherein $R^2$ and $R^3$ form a piperazinyl group may then be N-alkylated following art known N-alkylation procedures, e.g. reductive N-alkylation. The compounds of formula (I) wherein $R^2$ and $R^3$ form a piperazinyl group substituted with 2,3-dihydroxypropyl may be prepared by reacting the corresponding piperazine derivative substituted with 2,2-dimethyl-1,3-dioxolanylmethyl in the presence of an acid.

In all of the foregoing and in the following preparations, the reaction products may be isolated from the reaction mixture and, if necessary, further purified according to methodologies generally known in the art.

The intermediates of formula (II) can be prepared by cyclizing an intermediate of formula (III) upon catalytic hydrogenation in the presence of a suitable catalyst, e.g. palladium on charcoal, in a reaction-inert solvent, e.g. 2-methoxyethanol, acetic acid and the like.

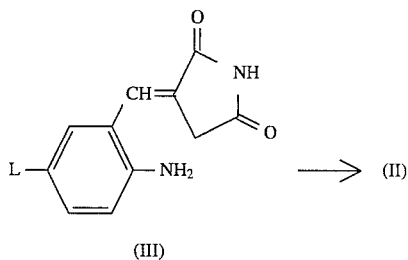

(III)

Alternatively, the intermediates of formula (II) can be prepared by cyclizing an intermediate of formula (IV) upon catalytic hydrogenation in the presence of a suitable catalyst, e.g. palladium on charcoal, in a reaction-inert solvent, e.g. ethanol, 2-methoxyethanol and the like.

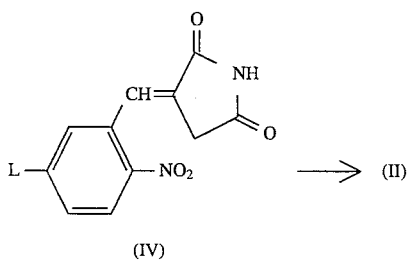

(IV)

The intermediates of formula (III) can be prepared upon catalytic hydrogenation of an intermediate of formula (IV) in the presence of a suitable catalyst, e.g. platinum on charcoal, in a reaction-inert solvent, e.g. 2-methoxyethanol and the like, preferably in the presence of a catalyst poison, e.g. thiophene.

The intermediates of formula (IV) can be prepared by reacting an intermediate of formula (V) with a phosphorus ylide of formula (VI) (Witrig reaction) in a reaction-inert solvent, e.g. ethanol, and the like.

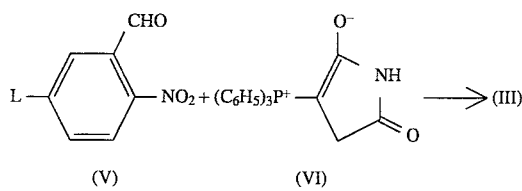

(V)                (VI)

The compounds of formula (I), the pharmaceutically acceptable addition salts and stereochemically isomeric forms thereof as well as the intermediates of formula (H), the pharmaceutically acceptable addition salts and stereochemically isomeric forms thereof, are potent inhibitors of the phosphodiesterase type III (cardiotonic-sensitive PDE IID of warm-blooded animals, in particular humans. Inhibition of PDE III leads to an elevation of cAMP in cardiac muscle, which in turn enhances sarcolemmal entry of $Ca^{2+}$ into the cell, increases the release and reuptake of $Ca^{2+}$ by the sarcoplasmic reticulum and probably also increases the sensitivity of contractile proteins to $Ca^{2+}$. As a result an increased contractile force of the heart ensues (positive inotropy) as well as a faster relaxation of the heart (positive lusitropy). Particularly important is the observation that the positive inotropic and lusitropic effects generally do not coincide with a simultaneous increase of other haemodynamic variables such as heart rate and blood pressure. Concommittant increases of heart rate and/or blood pressure would indeed put extra strain on the heart and cancel the beneficial positive cardiac inotropy and lusitropy. In vivo experiments with the instant compounds of formula (I) show moderate systemic vasodilation and hence a decrease in blood pressure. The heart rate generally only increases at high doses. In all, the instant compounds of formula (I) significantly increase cardiac output by cardiac positive inotropy and lusitropy and without major influence on heart rate and/or blood pressure.

Consequently, the compounds of formula (I) and (II) are considered to be valuable therapeutical drugs for treating warm-blooded animals, particularly humans, suffering from Congestive Heart Failure. Congestive Heart Failure is a pathophysiological state that is defined by the inability of the heart to pump adequate amounts of blood to the peripheral sites of the organism, with consequent failure to meet the metabolic requirement of the body. Said condition may result from a heart attack, infection of the heart, chronic hypertension, deficiencies in the operation of the heart valves and other disorders of the heart leading to Congestive Heart Failure.

Some of the subject compounds show the advantage of having improved water solubility when compared to the art compounds.

In view of their useful positive inotropic and lusitropic properties, the subject compounds may be formulated into various pharmaceutical forms tier administration purposes. To prepare the pharmaceutical compositions of this invention, an effective amount of the particular compound, in base or acid addition salt form, as the active ingredient is combined in intimate admixture with a pharmaceutically acceptable carrier, which may take a wide variety of forms depending on the form of preparation desired for administration. These pharmaceutical compositions are desirably in unitary dosage form suitable, preferably, for administration orally, rectally, percutaneously, or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wettable agent, optionally combined with suitable additives of any nature in minor proportions, which additives do not cause any significant deleterious effects on the skin. Said additives may facilitate the administration to the skin and/or may be helpful for preparing the desired compositions. These compositions may be administered in various ways, e.g. as a transdermal patch, as a spot-on or as an ointment. Addition salts of the compounds of formula (I) due to their increased water solubility over the corresponding base form, are obviously more suitable in the preparation of aqueous compositions.

It is especially advantageous to formulate the aforementioned pharmaceutical compositions in dosage unit form for ease of administration and uniformity of dosage. Dosage unit form refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions and the like, and segregated multiples thereof.

In view of the usefulness of the subject compounds in the treatment of Congestive Heart Failure it is evident that the present invention provides a method of treating warm-blooded animals suffering from Congestive Heart Failure, said method comprising the systemic administration of a pharmaceutically effective amount of a compound of formula (I) or (II) or a pharmaceutically acceptable addition salt thereof or a stereochemically isomeric form thereof in admixture with a pharmaceutical carrier. In general it is contemplated that an effective daily amount would be from 0.01 mg/kg to 4 mg/kg body weight, more preferably from 0.04 mg/kg to 2 mg/kg body weight.

It is evident that said effective daily amount may be lowered or increased depending on the response of the treated subject and/or depending on the evaluation of the physician prescribing the compounds of the instant invention. The effective daily amount ranges mentioned hereinabove are therefore guidelines only and are not intended to limit the scope or use of the invention to any extent.

The following examples are intended to illustrate and not to limit the scope of the present invention.
Experimental Part
A. Preparation of the Intermediates

EXAMPLE 1 a) A mixture of ethyl 5-(3-formyl-4-nitrophenoxy)pentanoate (0.60 mol) and (4,5-di-hydro-2-hydroxy-5-oxo-1H-pyrrol-3-yl)triphenylphosphonium, hydroxide, inner salt (0.57 mol) in ethanol (1500 ml) was stirred and refluxed for 1 hour. The solvent was removed. The residue was stirred in methylbenzene. The resulting precipitate was filtered off, washed with methylbenzene, 2,2'-oxybispropane and dried, yielding 137.3 g (61%) of (E)-ethyl 5-[3-[(2,5-dioxo-3-pyrrolidinylidene)methyl]-4-nitrophenoxy]pentanoate; mp. 112.4° C. (interm. 1).

In a similar manner there were prepared:

(E)-ethyl 4-[3-[(2,5-dioxo-3-pyrrolidinylidene)methyl]-4-nitrophenoxy]butanoate (interm. 2);

(E)-3-[(2-nitrophenyl)methylene]-2,5-pyrrolidinedione; top. 174.1° C. (interm. 3); ethyl (E)-[3-[(2,5-dioxo-3-pyrrolidinylidene)methyl]-4-nitrophenoxy]acetate; mp. 147.8° C. (interm. 9); and methyl (E)-6-[3-[(2,5-dioxo-3-pyrrolidinylidene)methyl]-4-nitrophenoxy]hexanoate (interm. 10).

b) A mixture of intermediate (1) (0.179 mol) in 2-methoxyethanol (600 ml) and thiophene, 4% solution (4 ml) was hydrogenated at 50° C. with platinum on activated carbon (5%) (8 g) as a catalyst. After uptake of the theoretical amount of hydrogen, the catalyst was filtered off. The precipitate, which was formed overnight, was filtered off, washed with ethyl acetate and 2,2'-oxybispropane and dried in vacuo, yielding 42.7 g of product. The filtrate was evaporated and the residue was stirred in ethyl acetate. The precipitate was filtered off, washed with ethyl acetate and 2,2'-oxybispropane and dried in vacuo yielding a second portion of product (13.8 g), which was crystallized from methoxyethanol, yielding 8.3 g. Total yield: 51 g (82.2%) of ethyl (E)-5-[4-amino-3-[(2,5-dioxo-3-pyrrolidinylidene)methyl]phenoxy]pentanoate; mp. 183.5° C. (interm. 4).

In a similar manner there was also prepared:

ethyl 4-[4-amino-3-[(2,5-dioxo-3-pyrrolidinylidene)methyl]phenoxy]butanoate; mp. 176.5° C. (interm. 5);

methyl (E)-6-[4-amino-3-[(2,5-dioxo-3-pyrrolidinylidene)methyl]phenoxy]hexanoate; mp. 178.4° C. (interm. 12); and ethyl (E)-[4-amino-3-[(2,5-dioxo-3-pyrrolidinylidene)methyl]phenoxy]acetate (interm. 13).

c) Intermediate (5) (0.06 mol) in acetic acid (250 ml) was hydrogenated at 50° C. with palladium on activated carbon (10%) (4 g) as a catalyst. After uptake of the theoretical amount of hydrogen, the catalyst was filtered off and washed with acetic acid. The filtrate was evaporated and the residue was boiled up in ethanol. The precipitate was filtered off, washed with ethanol, 2,2'-oxybispropane and dried in vacuo, yielding 15.2 g (80%) of ethyl 4-[(2,3,3a,4-tetrahydro-2-oxo-1H-pyrrolo[2,3-b]quinolin-6yl)oxy]butanoate (interm. 6).

EXAMPLE 2 b) A mixture of intermediate (1) (0.007 mol) in ethanol (150 ml) was hydrogenated at 50° C. and at normal pressure with palladium on activated carbon (10% ) (2 g) as a catalyst. After uptake of the theoretical amount of hydrogen, the catalyst was filtered off and the filtrate was evaporated. This fraction was stirred in boiling ethyl acetate, filtered off, washed with ethyl acetate and 2,2'-oxybispropane, and dried (vacuum), yielding 1.0 g (45%) of ethyl 5-[(2,3,3a,4-tetrahydro-2-oxo-1H-pyrrolo[2,3-b]quinolin-6yl)oxy]pentanoate; mp. 179.7° C. (interm. 7);

In a similar manner there was prepared:

ethyl 4-[(2,3,3a,4-tetrahydro-2-oxo-1H-pyrrolo[2,3-b]quinolin-6-yl)oxy]butanoate; mp. 177.1° C. (interm. 6);

methyl 6-[(2,3,3a,4-tetrahydro-2-oxo-1H-pyrrolo[2,3-b]quinolin-6-yl)oxy]hexanoate; mp. 199.3° C. (interm. 15); and ethyl [(2,3,3a,4-tetrahydro-2-oxo-1H-pyrrolo[2,3-b]quinolin-6-yl)oxy]acetate (interm. 16).

EXAMPLE 3

A solution of intermediate (3) (0.0215 mol) in acetic acid (150 ml) was hydrogenated under atmospheric conditions with palladium on activated carbon (10%) (2 g) as a catalyst. After uptake of the theoretical amount of hydrogen, the reaction mixture was stirred and refluxed for 4 hours ($H_2$ removal). Then, the catalyst was filtered off and the filtrate was evaporated. The residue was washed with 2-propanol (40 ml), then dried, yielding 2.53 g (64%) of 1,3-dihydro-2H-pyrrolo[2,3-b]quinolin-2-one; mp. 261.1° C. (interm. 8).
B. Preparation of the Final Compounds

EXAMPLE 4 a) A solution of intermediate (6) (0.0064 mol) in tetrahydrofuran (80 ml) was stirred at 70° C. (oil bath). 4,5-dichloro-3,6-dioxo-1,4-cyclohexadiene-1,2-dicarbonitrile (2.16 g) was added in one portion and the mixture was stirred for 5 minutes. A second portion of 4,5-dichloro-3,6-dioxo-1,4-cyclohexadiene-1,2-dicarbonitrile (0.00158 mol) was added and the reaction mixture was stirred for an additional 10 minutes. The solvent was evaporated. The residue was stirred in a mixture of $CH_2Cl_2/CH_3OH$ 90/10 and washed with water. Insoluble material was removed by filtration and the filtrate was evaporated.

The residue was purified by column chromatography over silica gel (eluent: $CH_2Cl_2/CH_3OH$ 95/5). The pure fractions were collected and the solvent was evaporated. The residue was stirred in boiling ethanol (30 ml). The precipitate was filtered off, washed with ethanol and 2,2'-oxybispropane and dried (vacuum; 60°–70° C.), yielding 0.76 g (38.1%) of ethyl 4-[(2,3-dihydro-2-oxo-1H-pyrrolo[2,3-b]quinolin-6-yl]oxy]butanoate; mp. 181.4° C. (comp. 1).

In a similar manner there was prepared:

ethyl 5-[(2,3-dihydro-2-oxo-1H-pyrrolo[2,3-b]quinolin-6-yl]oxy]pentanoate; mp. 180.9° C. (comp. 2).

b) A solution of compound (1) (0.0130 mol) in a mixture of sodium hydroxide 1N (0.040 mol) in ethanol (40 ml) was stirred at room temperature until the reaction was complete. Then, HCl 1N (40 ml) was added and the resulting mixture was concentrated under reduced pressure. The residue was stirred in water and the resulting precipitate was filtered off, washed with water and dried (vacuum; 70° C.). This fraction was stirred in boiling ethanol, filtered off, washed with ethanol and 2,2'-oxybispropane, then dried (vacuum 60°–70° C.), yielding 3.22 g (86.5%) of 4-[(2,3-dihydro-2-oxo-1H-pyrrolo[2,3-b]quinolin-6-yl)oxy]butanoic acid; mp. 260° C. (comp. 3).

In a similar manner there was prepared:

5-[(2,3-dihydro-2-oxo-1H-pyrrolo[2,3-b]quinolin-6-yl)oxy]pentanoic acid; mp.>260° C. (comp. 4);

6-[(2,3-dihydro-2-oxo-1H-pyrrolo[2,3-b]quinolin-6-yl)oxy]hexanoic acid (comp. 18); and

[(2,3-dihydro-2-oxo-1H-pyrrolo[2,3-b]quinolin-6-yl)oxy]acetic acid (comp. 19).

EXAMPLE 5

A mixture of intermediate (6) (0.06 mol), 2,5-dimethyl-2,4-hexadiene (40 g) in methylbenzene (400 ml) was heated overnight at 195° C. (closed vessel) in the presence of platinum on activated carbon (10%) (3 g) as a catalyst and a 4% solution of thiophene (2 ml). The mixture was cooled, filtered over dicalite and washed with methylbenzene. The precipitate was stirred in a mixture of dichloromethane and acetic acid (50/50) and filtered over dicalite. The filtrate was evaporated and the residue was stirred in boiling ethanol, filtered off, washed and dried in vacuo, yielding 14.5 g (77%) of ethyl 4-[(2,3-dihydro-2-oxo-1H-pyrrolo[2,3-b]quinolin-6-yl)oxy]butanoate (comp. 1).

In a similar manner was prepared:

ethyl 5-[(2,3-dihydro-2-oxo-1H-pyrrolo[2,3-b]quinolin-6-yl)oxy]pentanoate (comp. 2);

methyl 6-[(2,3-dihydro-2-oxo-1H-pyrrolo[2,3-b]quinolin-6-yl)oxy]hexanoate (comp. 20);

ethyl [(2,3-dihydro-2-oxo-1H-pyrrolo[2,3-b]quinolin-6-yl)oxy]acetate (comp. 21).

EXAMPLE 6

Diphenyl phosphoryl azide (0.0085 mol) was added to a mixture of compound (3) (0.0059 mol), 1-(cyclohexanylmethyl)piperazine (0.0072 mol), N,N-diethylethanamine (0.0124 mol) and N,N-dimethyl-4-pyridinamine (catalytic quantity) in N,N-dimethylformamide (30 ml), stirred at room temperature. The reaction mixture was stirred overnight at room temperature. Dichloromethane (200 ml) was added and the mixture was washed with water. The organic layer was dried, filtered and the solvent was evaporated. The residue was stirred in boiling methanol (20 ml). The precipitate was filtered off, washed with methanol and 2,2'-oxybispropane, then dried. This fraction (1.5 g) was dissolved in a mixture of methanol/methanol($NH_3$)/ trichloromethane (5/5/90) and filtered over silica gel column. The desired fractions were collected and the solvent was evaporated. The residue was stirred in boiling methanol (20 ml), filtered off, washed with methanol, 2,2'-oxybispropane and dried in vacuo at 60° C., yielding 1.36 g (51.2%) of 1-(cyclohexylmethyl)-4-[4-[(2,3-dihydro-2-oxo-1H-pyrrolo[2,3-b]quinolin-6-yl)oxy]-1-oxobutyl]piperazine; mp. 227.2° C. (comp. 5).

In a similar manner there were prepared:

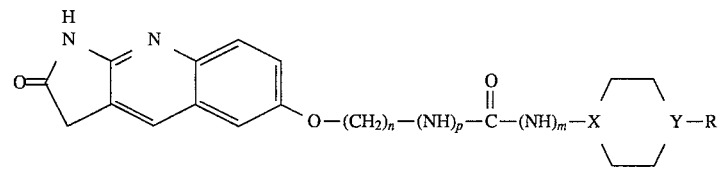

| Comp. No. | n | p | m | X | Y | R | physical data/salts (mp. in °C.) |
|---|---|---|---|---|---|---|---|
| 6 | 4 | 0 | 0 | N | N | cyclohexylmethyl | 194.7 |
| 7 | 4 | 0 | 1 | C | N | phenylmethyl | 234.0 |
| 9 | 3 | 0 | 0 | N | N | 1-butyl | 198.4 |
| 10 | 3 | 0 | 0 | N | N | phenylmethyl | 221.8 |
| 11 | 3 | 0 | 0 | N | N | cyclohexyl | .2HCl.½$H_2O$ |
| 12 | 3 | 0 | 0 | N | C | 1H-imidazol-2-ylcarbonyl | 255.0 |
| 13 | 3 | 0 | 0 | N | N | 2-pyridinyl | 249.1 |
| 14 | 3 | 0 | 0 | N | N | 2-pyrimidinyl | 260 |
| 22 | 4 | 0 | 0 | N | N | phenylmethyl | 206.8 |
| 23 | 3 | 0 | 0 | N | N | diphenylmethyl | 230.0 |
| 24 | 4 | 0 | 0 | N | N | 1-butyl | 178.9 |
| 25 | 4 | 0 | 0 | N | N | cycloheptyl | 192.8 |

-continued

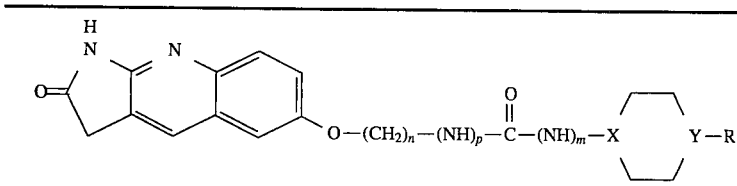

| Comp. No. | n | p | m | X | Y | R | physical data/salts (mp. in °C.) |
|---|---|---|---|---|---|---|---|
| 26 | 5 | 0 | 0 | N | N | cyclohexylmethyl | 193.2 |
| 27 | 3 | 0 | 0 | N | N | 4-methoxyphenyl | 218.6 |
| 28 | 1 | 0 | 0 | N | N | cyclohexylmethyl | 244.7 |
| 29 | 4 | 1 | 0 | N | N | cyclohexylmethyl | 170.5 |
| 30 | 4 | 0 | 1 | C | N | cyclohexylmethyl | 220.6 |
| 31 | 4 | 0 | 0 | N | N | (4-chlorophenyl)methyl | 234.6 |
| 32 | 3 | 0 | 0 | N | N | $-CH_2-\begin{smallmatrix}CH_3\ \ CH_3\\ \diagdown\diagup\\O\ \ \ O\end{smallmatrix}$ | 209.0 |
| 33 | 3 | 1 | 0 | N | N | cyclohexylmethyl | 209.7 | and 4-[(2,3-dihydro-2-oxo-1H-pyrrolo[2,3-b ]quinolin-6-yl)oxy]-N-methyl-N-(1-methyl-4-piperidinyl)butanamide; mp. 212.4° C. (comp. 8).

b) Compound (6) (0.0033 mol) was stirred in boiling ethanol (20 ml). This mixture was acidified with HCl/2-propanol. The mixture was cooled. The precipitate was filtered off, washed with ethanol, 2,2'-oxybispropane and dried (vacuum), yielding 1.40 g (84.7%) of 1-(cyclohexylmethyl)-4-[5-[(2,3-dihydro-2-oxo-1H-pyrrolo[2,3-b]-quinolin-6-yl)oxy]-1-oxopentyl]piperazine monohydrochloride; mp. 271.8° C. (comp. 15).

In a similar manner there was prepared:

1-(cyclohexylmethyl)-4-[4-[(2,3-dihydro-2-oxo- 1H-pyrrolo[2,3-b]quinolin-6-yl)oxy]-1-oxobutyl]piperazine dihydrochloride ethanolate(1:1); mp. 204.8° C. (comp. 16).

EXAMPLE 7

Thionyl chloride (0.00803 mol) was added dropwise to a suspension of compound (3) (0.0073 mol) in N,N-dimethylformamide (25 ml). The mixture was stirred for 5 minutes. Then, N-methyl-cyclohexanamine (0.0438 mol) was added in one portion and the reaction mixture was further stirred at room temperature. The solvent was evaporated. The residue was taken up in $CH_2Cl_2/CH_3OH$ (90/10) and washed with water. The separated organic layer was dried ($MgSO_4$), filtered and the solvent was evaporated. The residue was purified by column chromatography over silica gel (eluent: $CHCl_3/(CH_3OH/NH_3)$/tetrahydrofuran 90/5/5). The eluent of the desired fraction was evaporated and the residue (0.4 g) was crystallized from ethanol. The precipitate was filtered off, washed with a small amount of ethanol, 2,2'-oxybispropane and dried (vacuum; 60° C.), yielding 0.150 g (5.3%) of N-cyclohexyl-4-[(2,3-dihydro-2-oxo-1H-pyrrolo[2,3-b] quinolin-6-yl)oxy]-N-methylbutanamide hemihydrate; mp. 203.9° C. (comp. 17).

EXAMPLE 8 a) A mixture of compound 10 (0.0078 mol) in 2-methoxyethanol (250 ml) was hydrogenated at 50° C. with palladium on activated carbon, palladium content 10% (1 g) as a catalyst. After uptake of $H_2$ (1 equiv), the catalyst was filtered off and the filtrate was evaporated. The residue was stirred in boiling ethyl acetate, filtered off, washed with ethyl acetate and dried (vacuum), yielding 2.4 g (87%) of 1-[4-[(2,3-dihydro-2-oxo-1H-pyrrolo[2,3-b]quinolin-6-yl)oxy]-1-oxobutyl]piperazine (comp. 35).

b) A mixture of compound 35 (0.0067 mol) and 3-cyclopentyloxy-4-methoxybenzaldehyde (0.0091 mol) in 2-methoxyethanol (150 ml) was hydrogenated at 50 ° C. with palladium on activated carbon, palladium content 10% (2 g) as a catalyst in the presence of thiophene, 4% solution (1 ml). After uptake of $H_2$ (1 equiv), the catalyst was filtered off and the filtrate was evaporated. The residue was purified by column chromatography over silica gel (eluent: $CH_2Cl_2/CH_3OH$ 94/6). The pure fractions were collected and the solvent was evaporated. The residue was stirred in boiling ethanol. The precipitate was filtered off, washed with ethanol and DIPE, then dried (vacuum), yielding 0.62 g (16.6%) 1-[[3-(cyclopentyloxy)-4-methoxyphenyl]methyl]-4-[4-[(2, 3-dihydro-2-oxo-1H-pyrrolo[2,3-b]quinolin-6-yl)oxy]-1-oxobutyl]piperazine; mp. 4.1° C. (comp. 36).

EXAMPLE 9

A mixture of compound 32 (0.0085 mol) in acetic acid (95 ml) was stirred for 10 hours at 60° C. The solvent was evaporated. The residue was stirred in water and this mixture was alkalized with an aqueous ammonia solution. The water layer was separated and extracted with $CH_2Cl_2/CH_3OH$ 90/10. The separated organic layer was dried ($MgSO_4$), filtered and the solvent was evaporated. The residue was purified by column chromatography over silica gel (eluent: $CH_2Cl_2/(CH_3OH/NH_3)$90/10). The pure fractions were collected and the solvent was evaporated. The residue was stirred in DIPE, filtered off, washed and vacuum dried, yielding 1.05 g (28.2%) (±)-4-[4-[(2,3-dihydro-2-oxo-1H-pyrrolo[2,3-b]quinolin-6-yl)oxy]- 1-oxobutyl]-β-hydroxy-1-piperazinepropanol hemihydrate; top. 219.7° C. (comp. 37).

C. Pharmacological Examples

The positive inotropic and lusitropic effect of the instant compounds was assessed by an in vitro assay system to detect inhibiting effect on the phosphodiesterase type III and in an in vivo experiment in closed-chest anesthetized dogs by monitoring cardiac and haemodynamic effects of an intravenous bolus injection of the instant compounds.

EXAMPLE 10: Inhibition of Phosphodiesterase Type III (PDE III)

Phosphodiesterase activity was measured in an incubation medium (200 μl) containing 40 mM Tris, 5 mM $MgCl_2$, 3.75 mM 2-mercaptoethanol, [$^3$H]cAMP and [$^3$H]cGMP (310 mCi/mmol) at pH 7.1. For every preparation, time- and concentration-dependent changes in cyclic nucleotide hydrolysis were measured. From these data, a protein concentration was chosen that showed a linear increase in phosphodiesterase activity during an incubation period of 10 min at 37° C. The enzymatic activity was started by addition of substrate and stopped 10 min later after the tubes were transferred to a waterbath at 100° C. for 40 sec. After the tubes had been cooled to room temperature, alkaline phosphatase (0.25 g/ml) was added and the mixture was left at 37° C. for 20 min. The mixture was subsequently applied to a 1-ml DEAE-Sephadex A-25 column and washed twice with 3 ml of 20 mM Tris-HCl at pH 7.4. The $^3$H-labeled reaction products in the eluate were quantified by liquid scintillation counting. The inhibiting effect of the present compounds on canine heart phosphodiesterase PDE III was measured at different concentrations of the instant compounds. The $IC_{50}$ values were calculated graphically from the thus obtained inhibition values. Table 1 shows available $IC_{50}$ values of the present compounds on canine heart PDE III.

TABLE 1

| Comp. No. | Canine heart PDE III $IC_{50}$ $(10^{-6}$ M) |
| --- | --- |
| 1 | 0.29 |
| 2 | 0.062 |
| 3 | 0.33 |
| 5 | 0.018 |
| 6 | 0.0024 |
| 7 | 0.058 |
| 8 | 0.30 |
| 15 | 0.0018 |
| 16 | 0.027 |
| 17 | 0.0076 |

EXAMPLE 11

Positive Inotropy and Lusitropy, Blood Pressure and Heart Rate in Dogs

The test compound was dissolved in an aqueous glucose solution in a concentration of 1 mg.ml$^{-1}$. The experiments were performed on 3 Beagle dogs of either sex and varying age, ranging in body weight from 11 to 18 kg (median 13 kg). The animals were intravenously anaesthetized with a mixture of 0.015 mg.kg$^{-1}$ scopolamine and 0.05 mg.kg$^{-1}$ lofentanil. The animals were intubated with a cuffed endotracheal tube. Intermittent positive pressure ventilation was performed with a mixture of pressurized air and oxygen (60/40), using a volume-controlled ventilator (Siemens Elema). In the control period the $CO_2$ concentration in the expired air (ET $CO_2$), as determined with a capnograph (Gould Godart), was kept at 5 vol % by adjustment of the respiratory volume (resp. rate=20 breaths.min$^{-1}$). A continuous intravenous infusion of 0.5 mg.kg$^{-1}$.h$^{-1}$ of etomidate was started immediately after induction. Body temperature was monitored with a thermistor positioned in the pulmonary artery. To prevent blood clotting heparin, 1000 IU.kg$^{-1}$ i.v., was administered.

The electrocardiogram (ECG) was derived from limb leads (standard lead 2). Left ventricular (LVP) and ascending aortic blood pressure (AoP) were measured by retrograde catheterisation via the femoral arteries with high fidelity cathetertip micromanometers (Honeywell). The other femoral vein was cannulated for injection of saline at room temperature into the right atrium and for injection of the test compound. Peak ascending aortic blood flow velocity was measured through the fight carotid artery with an electomagnetic catheter-tip probe connected to a square wave electomagnetic flow meter (Janssen Scientific Instruments). The following variables—inter alia—were calculated on-line, usually at 1 rain intervals: heart rate (HR), diastolic (AoPd) aortic blood pressure, left ventricular end-diastolic pressure (LVEDP), the maximum positive and maximum negative rate of change of isovolumic LVP (LV dp/dt$_{max}$ and $_{min}$, respectively), the maximum positive first derivative divided by the actually developed pressure in the left ventricle (LV dp/dt$_{max}$/Pd). The time constant (T) of relaxation was measured with the use of an exponential analysis that also estimated the asymptote. After a stabilization period, the animals were treated by intravenous bolus injection of the test compound at 30 min. interval in cumulative doses of 0.0005, 0.001, 0.004, 0.016, 0.064, 0.125 and 0.25 mg/kg.

The test compounds have positive inotropic properties as indicated by the pronounced and significant increase in the variables related to cardiac performance (LV dp/dt$_{max}$, LV dp/dt$_{max}$/Pd). The test compounds have positive lusitropic properties, as evidenced by the significant decrease in the time constant of relaxation. Upon administration of the test compounds, systemic and pulmonary peripheral vascular resistance decrease significantly. This indicates that the test compounds have also additional systemic and pulmonary vasodilatory properties. This unloading of the heart occurs without altering heart rate, but with concomitant increase in cardiac output. These positive inotropic and lusitropic, and vasodilatory effects of the compounds are long-lasting, since the changes in the variables last for more than 30 min after the bolus injection.

Table 2 shows the changes in haemodynamic variables measured 5 minutes after cumulative intravenous bolus administration of some of the present compounds in Beagle dogs. The variable AoPd (diastolic aortic blood pressure) shows the decrease in blood pressure (vasodilation), HR the influence of the present compounds on the heart rate, LV dp/dt$_{max}$ (the maximum positive rate of change of isovolumic left ventricular pressure) shows the positive inotropic effect.

TABLE 2

Calculated dose (in mg/kg i.v.) producing a 30% increase in cardiac contractility (LV dp/dt max), a 30% increase in heart rate (HR), a 15% reduction in diastolic aortic blood pressure (AoPD) and a 15% reduction of total systemic vascular resistance (TSR) relative to premedication values at 5 min after the i.v. administration to anaesthetized, closed-chest dogs (n = 3 for each compound).

| Co. No. | HR | AoPD | LV dp/dt$_{max}$ | TSR |
| --- | --- | --- | --- | --- |
| 15 | 0.028 | 0.015 | 0.002 | 0.003 |
| 5 | 0.033 | >0.25 | 0.008 | 0.079 |

D. Composition Examples

"Active ingredient" (A.I.) as used throughout these examples relates to a compound of formula (I) or (II), a pharmaceutically acceptable addition salt thereof or a stereochemically isomeric form thereof.

EXAMPLE 12: ORAL DROPS

500 Grams of the A.I. was dissolved in 0.5 l of 2-hydroxypropanoic acid and 1.5 l of the polyethylene glycol at 60–80° C. After cooling to 30–40° C. there were added 35 l of polyethylene glycol and the mixture was stirred well. Then there was added a solution of 1750 grams of sodium saccharin in 2.5 l of purified water and while stirring there were added 2.5 l of cocoa flavor and polyethylene glycol q.s. to a volume of 50 l , providing an oral drop solution comprising 10 mg/ml of A.I.. The resulting solution was filled into suitable containers.

EXAMPLE 13: ORAL SOLUTION

9 Grams of methyl 4-hydroxybenzoate and 1 gram of propyl 4-hydroxybenzoate were dissolved in 4 l of boiling purified water. In 3 l of this solution were dissolved first 10 grams of 2,3-dihydroxybutanedioic acid and thereafter 20 grams of the A.I. The latter solution was combined with the remaining part of the former solution and 12 l 1,2,3-propanetriol and 3 l of sorbitol 70% solution were added thereto. 40 Grams of sodium saccharin were dissolved in 0.5 l of water and 2 ml of raspberry and. 2 ml of gooseberry essence were added. The latter solution was combined with the former, water was added q.s. to a volume of 20 l providing an oral solution comprising 5 mg of the active ingredient per teaspoonful (5 ml). The resulting solution was filled in suitable containers.

EXAMPLE 14: CAPSULES

20 Grams of the A.I., 6 grams sodium lauryl sulfate, 56 grams starch, 56 grams lactose, 0.8 grams colloidal silicon dioxide, and 1.2 grams magnesium stearate were vigorously stirred together. The resulting mixture was subsequently filled into 1000 suitable hardened gelatin capsules, comprising each 20 mg of the active ingredient.

EXAMPLE 15: FILM-COATED TABLETS

Preparation of tablet core

A mixture of 100 grams of the A.I., 570 grams lactose and 200 grams starch was mixed well and thereafter humidified with a solution of 5 grams sodium dodecyl sulfate and 10 grains polyvinylpyrrolidone (Kollidon-K 90 ®) in about 200 ml of water. The wet powder mixture was sieved, dried and sieved again. Then there was added 100 grams microcrystalline cellulose (Avicel ®) and 15 grams hydrogenated vegetable oil (Sterotex ®). The whole was mixed well and compressed into tablets, giving 10.000 tablets, each containing 10 mg of the active ingredient.
Coating To a solution of 10 grams methyl cellulose (Methocel 60 HG®) in 75 ml of denaturated ethanol there was added a solution of 5 grams of ethyl cellulose (Ethocel 22 cps ®) in 150 ml of dichloromethane. Then there were added 75 ml of dichloromethane and 2.5 ml 1,2,3-propanetriol. 10 Grams of polyethylene glycol was molten and dissolved in 75 ml of dichloromethane. The latter solution was added to the former and then there were added 2.5 grams of magnesium octadecanoate, 5 grams of polyvinylpyrrolidone and 30 ml of concentrated colour suspension (Opaspray K-1-2109®) and the whole was homogenated. The tablet cores were coated with the thus obtained mixture in a coating apparatus.

EXAMPLE 16: INJECTABLE SOLUTION 1.8 Grams methyl 4-hydroxybenzoate and 0.2 grams propyl 4-hydroxybenzoate were dissolved in about 0.5 l of boiling water for injection. After cooling to about 50° C. there were added while stirring 4 grams lactic acid, 0.05 grams propylene glycol and 4 grams of the A.I.. The solution was cooled to room temperature and supplemented with water for injection q.s. ad 1l, giving a solution comprising 4 mg/ml of A.I.. The solution was sterilized by filtration (U.S.P. XVII p. 811 ) and filled in sterile containers.

We claim:

1. A compound having the formula

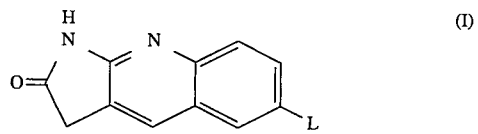

a pharmaceutically acceptable addition salt thereof or a stereochemically isomeric form thereof, wherein L is a radical of formula $-O-Alk-(NH)_p-C(=O)-R^1$, wherein Alk is $C_{1-6}$alkanediyl;

p is 0 or 1; and $R^1$ is hydroxy, $C_{1-4}$alkyloxy or $-NR^2R^3$, wherein $R^2$ is hydrogen or $C^{1-4}$alkyl; and $R^3$ is $C_{3-7}$cycloalkyl or piperidinyl, which is optionally substituted with $C_{1-4}$alkyl or phenylmethyl or $C_{3-7}$cycloalkylmethyl;

$R^2$ and $R^3$ may also be joined together to form piperazinyl, optionally substituted with $C_{3-7}$cycloalkyl, $C_{3-7}$cycloalkylmethyl, $C_{1-6}$alkyl optionally substituted with one or two hydroxy groups, 2,2-dimethyl-1,3-dioxolanylmethyl, benzyl, halophenylmethyl, (cyclopentyloxy)(methoxy)phenylmethyl, diphenyl$C_{1-4}$alkyl, pyridinyl, pyrimidinyl or phenyl optionally substituted with $C_{1-4}$alkyloxy or halo; or $R^2$ and $R^3$ are joined together to form piperidinyl, optionally substituted with imidazolylcarbonyl.

2. A compound according to claim 1 wherein $R^1$ is $-NR^2R^3$.

3. A compound according to claim 2 wherein $R^2$ and $R^3$ are joined together to form a piperazinyl substituted with $C_{3-7}$cycloalkylmethyl.

4. A compound according to claim 3 wherein the compound is 1-(cyclohexylmethyl)-4-[4-[(2,3-dihydro-2-oxo-1H-pyrrolo[2,3-b]quinolin-6-yl)oxy]-1-oxobutyl]piperazine or 1-(cyclohexylmethyl)-4-[5-[(2,3-dihydro-2-oxo-1H-pyrrolo[2,3-b]quinolin-6-yl)oxy]-1-oxopentyl]piperazine, a pharmaceutically acceptable addition salt thereof or a stereochemically isomeric form thereof.

5. A compound having the formula

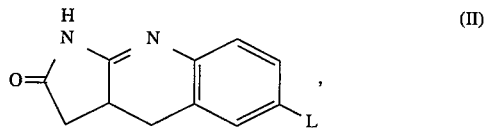

an addition salt thereof or a stereochemically isomeric form thereof, wherein L is as defined for the compounds of formula (I) in claim 1.

6. A compound having the formula

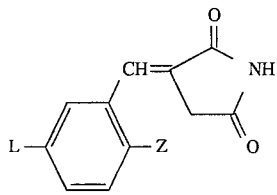

an addition salt thereof or a stereochemically isomeric form thereof wherein L is as defined for the compounds of formula (I) in claim 1 and Z is nitro or amino.

7. A pharmaceutical composition comprising a pharmaceutically acceptable carrier and as active ingredient an effective positive inotropic and lusitropic amount of a compound as defined in claim 1.

8. A pharmaceutical composition comprising a pharmaceutically acceptable carrier and as active ingredient an effective positive inotropic and lusitropic amount of a compound as defined in claim 2.

9. A pharmaceutical composition comprising a pharmaceutically acceptable carrier and as active ingredient an effective positive inotropic and lusitropic amount of a compound as defined in claim 3.

10. A pharmaceutical composition comprising a pharmaceutically acceptable carrier and as active ingredient an effective positive inotropic and lusitropic amount of a compound as defined in claim 4.

11. A method for treating congestive heart failure in warm blooded animals which comprises administering to warm blooded animals suffering from congestive heart failure an effective positive inotropic and lusitropic amount of a compound as defined in claim 1.

12. A method for treating congestive heart failure in warm blooded animals which comprises administering to warm blooded animals suffering from congestive heart failure an effective positive inotropic and lusitropic amount of a compound as defined in claim 2.

13. A method for treating congestive heart failure in warm blooded animals which comprises administering to warm blooded animals suffering from congestive heart failure an effective positive inotropic and lusitropic amount of a compound as defined in claim 3.

14. A method for treating congestive heart failure in warm blooded animals which comprises administering to warm blooded animals suffering from congestive heart failure an effective positive inotropic and lusitropic amount of a compound as defined in claim 4.

* * * * *